United States Patent [19]

Bow et al.

[11] 4,402,569

[45] Sep. 6, 1983

[54] OPTICAL FIBRE LIGHT GUIDES FOR USE WITH LASERS

[75] Inventors: Charles R. Bow, Glasgow; Ronald J. Burston, Troon, both of Scotland

[73] Assignee: Barr & Stroud Limited, Glasgow, Scotland

[21] Appl. No.: 267,732

[22] Filed: May 28, 1981

[30] Foreign Application Priority Data

May 31, 1980 [GB] United Kingdom ............. 8017864

[51] Int. Cl.³ .................................................. G02B 5/17
[52] U.S. Cl. .................................... 350/96.26; 350/227
[58] Field of Search ............ 350/96.26, 96.10, 96.24, 350/96.25, 96.23; 128/4–9

[56] References Cited

U.S. PATENT DOCUMENTS 3,690,769  9/1972  Mori .............................. 350/96.26
4,042,823  8/1977  Decker et al. ................. 350/96.26
4,170,997  10/1979  Pinnow et al. ................. 350/96.26

Primary Examiner—David K. Moore
Attorney, Agent, or Firm—Mason, Fenwick & Lawrence

[57] ABSTRACT

A laser photocoagulator 10, comprises a fibre optic guide 13 one end of which is accommodated by an endoscope 14 and the other end of which has a coupling 18 for connection to a laser 11 and a gas supply 12. Launch optics 32 are accurately located in coupling 18 with respect to end 34A of optical fibre 34 which traverses the length of the guide 13 thereby rendering the guide replaceable without dislocation of the endoscope 14, the laser 11 and the gas supply 12. The coupling 18 comprises separate clamp means for the optical fibre 34 and the optics 32 enabling accurate alignment co-axially and spatially so that the laser output is focussed on the free end 34A of the fibre 34 without any requirement to align the laser 11 accurately with optics 32.

6 Claims, 6 Drawing Figures

OPTICAL FIBRE LIGHT GUIDES FOR USE WITH LASERS

This invention relates to optical fibre light guides for use with lasers and to a laser photocoagulator incorporating such a guide.

Optical fibre light guides coupled to transmit the output of lasers used in medical applications, particularly in combination with endoscopes whereby the laser output is transmitted to a site within a patient. For application in photocoagulation of bleeding at such a site it is known to deliver laser energy to the site of the bleeding. In the known systems this is achieved with a single optical fibre forming part of a fibre-optic light guide which is an integral part of the laser and the endoscope and as a consequence should the optical fibre become damaged or contaminated sufficiently to degrade its performance it is necessary for the entire system to be removed from service to permit replacement of the delicate optical fibre by skilled personnel since the location of the ends of the optical-fibre is critical to correct functioning.

An object of the present invention is to provide an improved form of fibre-optic light guide for use with lasers.

According to the present invention there is provided a fibre-optic light guide for use with lasers, comprising a tubular housing containing a single optical fibre the ends of which are secured to the housing by clamp means, and wherein one end of said housing incorporates a lens arrangement for delivering focussed radiation to the pertaining end of the optical fibre, said one end of the housing being in the form of a coupling for attachment to a laser.

The present invention also provides a laser photocoagulator comprising a laser mounted on a support having a coupling member adjacent the radiation output of the laser and a fibre-optic light guide according to the preceding paragraph with said coupling releasably connected to said coupling member.

Conveniently the laser is Neodymium/YAG continuous wave (CW) and arranged to provide a substantially parallel output beam to the light guide. Conveniently also the light guide coupling actuates an interlock which prevents lasing of the laser when the coupling is released from the coupling member. Preferably the laser forms part of a system incorporating a pressurised gas source interconnected with an outlet port in said coupling member and said couplling incorporates a gas inlet port for receiving pressurised gas from said coupling member and delivering said gas to the other end of said tubular housing.

Conveniently said tubular housing is adapted for releasable attachment to an endoscope. Said attachment may incorporate an interlock which prevents lasing of the laser when the housing is released from the endoscope.

Embodiments of the present invention will now be described by way of example with reference to the accompanying drawings, in which:

FIG. 1 schematically illustrates in exploded form a laser coagulator incorporating the present invention;

Figure 1:
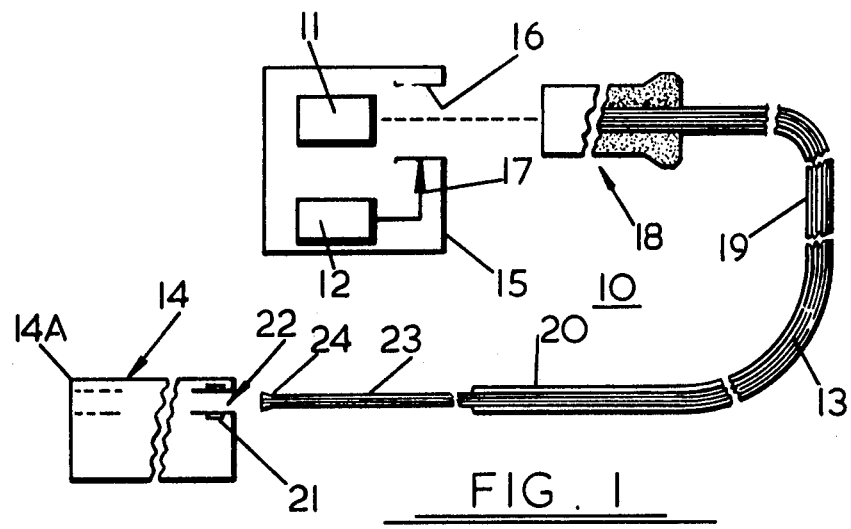

FIG. 1 illustrates in exploded form a partially schematically a laser photocoagulator 10 comprising a laser 11, a pressurised $CO_2$ gas supply 12, a flexible fibre-optic light guide 13 and a flexible endoscope 14. The laser 11 and the gas supply 12 are located within a housing 15 which acts as a support for these components and which has a coupling member 16 adjacent the radiation outlet of the laser 11. The gas supply 12 is in fluid connection with the coupling member 16 by means of a pipe 17. The guide 13 includes a tubular housing 19 as will be explained which at one end is in the form of a coupling 18 which is releasably securable to the coupling member 16. Part way along its length the housing 19 has an attachment 20 for mating with collar 21 fitted to the entry into a biopsy channel 22 within the endoscope 14. The end of the housing 19 remote from the coupling 18 is in the form of a catheter 23 which terminates in a tip 24, the length of the catheter 23 and tip 24 being such that when the photocoagulator is asssembled tip 24 is adjacent or slightly protruding from the endoscope end face 14A.

Figure 2:
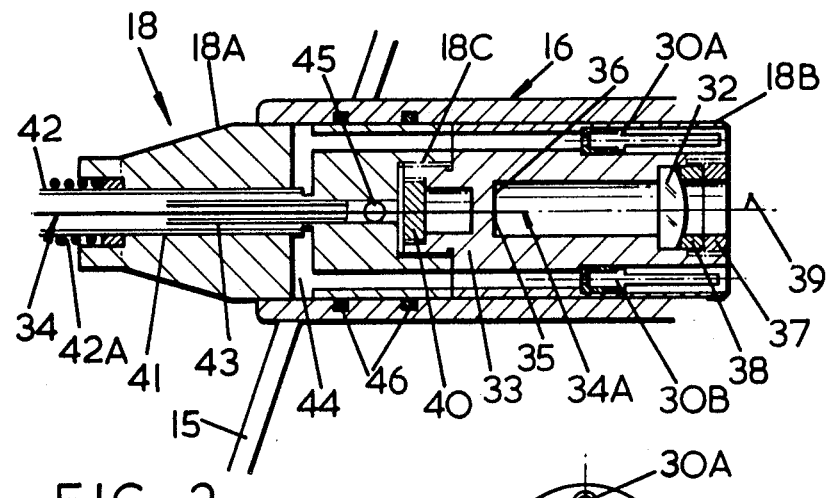
FIG. 2 illustrates part of a light guide used in FIG. 1.
Figure 3:
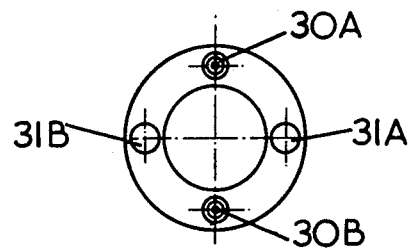
FIG. 3 is an end view of part of FIG. 2.

FIG. 2 illustrates in detail one form of the coupling 18 entered into the coupling member 16. Thus, the coupling member 16 is in the form of a cylindrical socket secured to the housing 15 and having its longitudinal axis aligned with the optical axis of the laser 11 contained within housing 15. The coupling 18 is in the form of a cylindrical spigot. When the spigot is push fitted into the socket four recesses in the free end face of the spigot engage corresponding pins in the socket two of which provide electrical connections and two of which provide for correct orientation of spigot and socket. As shown in FIGS. 2 and 3 recesses 30A, 30B are of small diameter and short in length and provide the electrical connections and recesses 31A, 31B are relatively large in diameter and long in length and provide for correct positioning of the spigot in the socket.

The coupling 18 as shown in FIG. 2 is formed in two parts 18A, 18B which are releasably secured together at screw threads 18C, part 18B containing the recesses 30A, 30B and 31A, 31B. Additionally part 18B contains a converging lens 32 mounted by means of a packing 38 and clamp ring 37. The lens 32 is planoconvex and the planar face thereof is in abutment with a mating planar face accurately formed in the part 18B. Additionally the cylindrical edge face of the lens 32 is accurately concentric with the optical axis of the lens and is mechanically an accurate fit with the mating cylindrical face in part 18B so that the lens 32 has its optical axis accurately aligned with the axis 39 of part 18B. Part 18B also incorporates a clamp arrangement 33 for the single optical fibre 34, being a fine tolerance hole 35 accurately co-axially located on web 36 and a screw-threaded collar 40 to which the fibre 34 is bonded. With this arrangement the end of the fibre 34 is accurately aligned co-axially with the lens 32 and the combination coarsely aligned with the laser output axis by virtue of the coupling 18 fitting approximately co-axially with the coupling member 16. Additionally however the fibre end face 34A is accurately located with respect to the focal point of lens 32.

Part 18A of coupling 18 is bonded at interface 41 to a flexible outer nylon tubing 42 which contains a flexible inner nylon tubing 43 within which is the fibre 34. A guard spring 42A prevents overflexing of the flexible tubing 42 as it emerges from coupling 18 which may lead to fracture of the fibre 34. The annular space between tubing 42 and tubing 43 communicates with the electrical connector recesses 30A, 30B, and permits electrical leads (not shown) to be taken to an electrical interlock at attachment 20. Additional electrical leads (not shown) may be taken to an interlock between the coupling 18 and the coupling member 16 so that in the event that either of these interlocks is not made the laser 11 is prevented from lasing.

The interlock at attachment 20 is in the form of an inductive coil contained in the housing 19 and a conductive ring located in collar 21 such that there is an overlap, and therefore the interlock is satisfied, for a small range of axial positions of the housing 19. This permits the guide tip 24 to have a small range of axial positions at the endoscope end 14A which is useful for medical purposes.

The annular space between tubing 43 and the fibre 34 communicates with a gas inlet orifice 45 in the part 18A which in turn leads to a corresponding outlet orifice (not shown) in coupling member 16 but located axially between O-ring seals 46 mounted on coupling member 16 and to which gas supply line 17 (FIG. 1) is lead.

Figure 4:
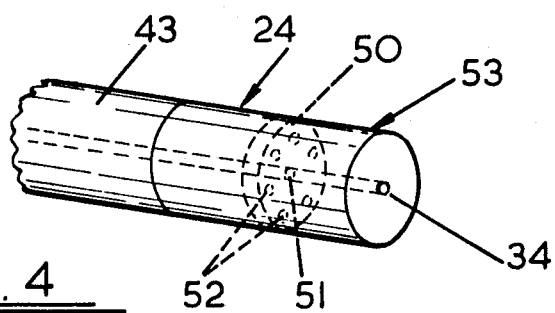
FIG. 4 illustrates another part of the light guide of FIG. 1.

One form of the end tip 24 of the catheter 23 is shown in FIG. 4 an comprises a web or plate 50 within a stainless steel tube 53 bonded to the end of the catheter tubing 43 having an axially located aperture 51 which acts as a clamp for the end of the fibre 34 and a series of six peripheral apertures 52 which act as nozzles for emission of the gas which aids the coagulation technique and keeps contaminants away from the tip of the fibre 34.

Figure 5:
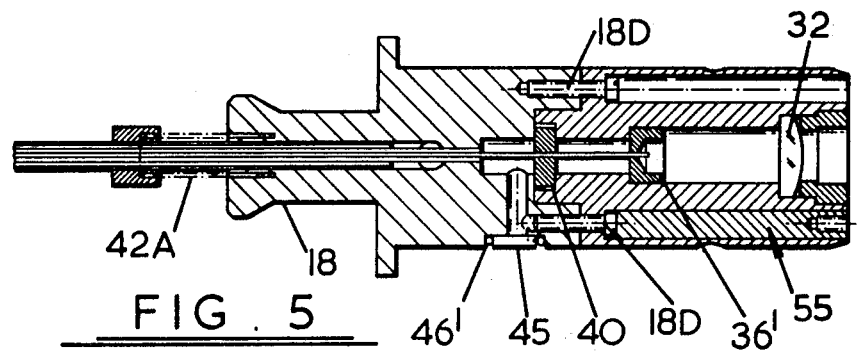
FIG. 5 illustrates an alternative to the FIG. 2 arrangement.

FIG. 5 illustrates another form of the coupling 18, functionally similar to that of FIG. 2 but differing in detail. The FIG. 5 coupling has a slightly different clamp arrangement 33 for the fibre 34 in that web 36 is replaced by a separate push-fit insert 36' whilst threaded collar 40 is retained. Also, instead of O-ring seals 46 being mounted on the fixed coupling member 16 these are replaced by a single O-ring seal 46' surrounding orifice 45 on the coupling 18. To provide unique angular orientation of coupling 18 relative to member 16 so that orifice 45 is aligned with the gas supply line orifie in member 16 only one orientation pin is provided in the socket corresponding to recess 31A the other recess 31B being blanked off by a nylon plug 55. To maintain unique orientation coupling parts 18A, 18B are not screw-threaded together but are united by means of bolts 18D.

Figure 6:
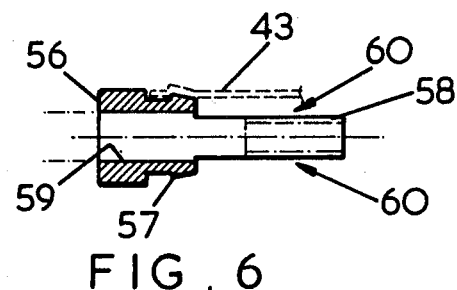
FIG. 6 illustrates an alternative to the FIG. 4 arrangement.

FIG. 6 shows a form of end tip 24 alternative to that of FIG. 4 and which comprises a spigot 56 for partial insertion into the end of nylon tubing 43. The spigot 56 has an annular catch edge 57 which grips the interior surface of tubing 43 so that bonding is avoided. Additionally a sleeve portion 58 of spigot 56 is provided to clamp the end of fibre 34, this portion 58 being partially cutaway at its periphery 60 to provide a continuation of the gas flow passageway within tubing 43, gas being emitted from the end face of spigot 56 by means of an oversize bore 59 communicating with the cutaway of portion 58.

It will be appreciated that a variety of gastrointestinal endoscopes 14 can be used with the laser system. Endoscopes used in other areas of the body can be interfaced to the laser. The laser system can be applied in non-endoscopic applications by using a plug-in fibre delivery system designed for the specific application, i.e. surgery, dermatology or ophthalmology. For one specific endoscope there can be a selection of fibres with different working characteristics i.e. beam divergence and termination tip combinations.

The fibre 34 is a glass-clad-glass fibre which has transmission characteristics and mechanical properties which conveniently enable the construction described above and permits the end face 34A of the fibre adjacent the lens 32 to be 'cleaved' so that this face can be made precisely parallel to the planar face of the lens 32 thereby permitting accuracy of launch of the laser beam into the fibre. It will be understood that the accuracy of positioning of fibre end face 34A and lens 32 and their co-axial alignment is measured in terms of microns whereas the lens 32 need not be located with such accuracy relative to the laser 11. The lens 32 need not be plano-convex provided that it is effective to converge the raw laser output beam into a focus at the fibre end face 34A. However it is particularly convenient to use a plano-convex lens because it simplifies the mechanical setting up and alignment procedure. It will also be noted that with the described embodiments should it become necessary to replace a degraded fibre 34 the guide 13 is releasable from the other components of the system and the fibre 34 is releasable from all parts of the guide 13 except collar 40 so that a replacement collar 40 is required on each renewal of fibre 34.

What is claimed is:

1. A fibre-optic guide for transmitting high power density light waveband radiation, comprising a flexible tubular housing containing a single optical fibre the ends of which are secured to the housing by clamp means, and wherein one end of the housing is in the form of a coupling for releasable attachment to a laser radiant-energy source, which coupling incorporates a lens arrangement accurately located therein for focussing collimated incident radiation onto the pertaining end of the optical fibre and the clamp means in said coupling fixedly locate said pertaining fibre end with respect to the lens arrangement for receiving said focussed radiation, wherein the clamp means in the coupling comprises a collar bonded to the fibre and releasably secured to the coupling and the clamp means at the other end of the housing comprises a member secured to the housing and having an aperture in which the adjoining end of the fibre is fitted whereby the fibre and collar are together rendered replaceable in the guide.

2. A guide as claimed in claim 1, wherein the fibre is glass-clad glass the end of which adjacent the lens arrangement is cleaved.

3. A guide as claimed in claim 1, wherein said coupling comprises means for directing a gas flow along said housing co-axially with said optical fibre and the other end of said housing comprises means for emitting said gas from said housing in a flow stream directed to keep the adjoining end of the fibre free of contaminants.

4. A guide as claimed in claim 3, wherein the coupling is formed by inter-engaged first and second parts and the fibre extends through said first part into said second part, which second part contains the clamp means and the lens arrangement and said first part comprises an orifice for receiving a supply or pressurised gas and leading to said gas flow directing means.

5. A guide as claimed in claim 1, wherein the fibre is glass-clad and liquid free.

6. A laser photocoagulator comprising a laser mounted on a support having a coupling member adjacent the radiation output of the laser, a fibre optic light guide as claimed in claim 1 with the coupling thereof releasably connected to said coupling member, and an endoscope accommodating the free end of said tubular housing, the tubular housing incorporating an interlock connected to prevent lasing operation of said laser except when said interlock is enabled by correct positioning of the endoscope with respect to the tubular housing.

* * * * *